US008501226B2

(12) United States Patent
Jepsen et al.

(10) Patent No.: US 8,501,226 B2
(45) Date of Patent: *Aug. 6, 2013

(54) COATING METHOD

(75) Inventors: Svenn Klüver Jepsen, Holte (DK); Gudrun Lasskogen, Hvidovre (DK)

(73) Assignee: Ferring B.V., Hoofdorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,511

(22) Filed: Sep. 7, 2012

(65) Prior Publication Data

US 2012/0328698 A1    Dec. 27, 2012

Related U.S. Application Data

(63) Continuation of application No. 10/583,669, filed as application No. PCT/EP2004/053537 on Dec. 16, 2004, now Pat. No. 8,282,958.

(60) Provisional application No. 60/531,682, filed on Dec. 23, 2003.

(30) Foreign Application Priority Data

Dec. 23, 2003  (EP) .................................... 03029598

(51) Int. Cl.
*A61K 9/00* (2006.01)
*A61K 9/14* (2006.01)
*A61K 9/36* (2006.01)
*A61K 31/196* (2006.01)
*A61K 9/48* (2006.01)
*B05D 5/00* (2006.01)
*A61P 1/00* (2006.01)
*A61P 1/04* (2006.01)

(52) U.S. Cl.
USPC ........... 424/463; 424/400; 424/480; 424/495; 514/567; 427/2.21

(58) Field of Classification Search
None
See application file for complete search history.

(56) References Cited

U.S. PATENT DOCUMENTS 5,188,841 A   2/1993   Simpkin et al.
5,254,347 A   10/1993  Samejima et al.
(Continued)

FOREIGN PATENT DOCUMENTS

EP   0148811 A1   7/1985
EP   0 540 813    5/1993
(Continued)

OTHER PUBLICATIONS

Klein et al., "Drug Release Characteristics of Different Mesalazine Products Using USP Apparatus 3 to Simulate Passage Through the GI Tract," *Dissolution Technologies*, Article 1, Nov. 2002, http://www.dissolutiontech.com/DTresour/1102art/1102_art1.htm, accessed on Dec. 12, 2010.

(Continued)

*Primary Examiner* — Robert A Wax
*Assistant Examiner* — William Craigo
(74) *Attorney, Agent, or Firm* — Foley & Lardner LLP

(57) ABSTRACT

The present invention concerns a method for coating granules comprising mesalazine, with a coating mixture comprising two polymers, polymer I and polymer II; said polymer I being selected to allow formation of a closing membrane around said granules in the absence of said polymer II, and said polymer II being selected to act as a water-soluble pore former in said coating mixture; wherein a) the amount of polymer I is adjusted to provide a closing membrane in the absence of polymer II, and b) the amount of polymer II in said coating mixture is adjusted to obtain coated granules which exhibit controlled release of mesalazine. The invention further concerns a product obtainable by the coating method.

18 Claims, 1 Drawing Sheet

U.S. PATENT DOCUMENTS

| | | |
|---|---|---|
| 5,472,712 A | 12/1995 | Oshlack et al. |
| 5,484,605 A | 1/1996 | Scheiffele et al. |
| 6,245,351 B1 | 6/2001 | Nara et al. |
| 7,022,345 B2 | 4/2006 | Valducci |
| 2001/0046964 A1 | 11/2001 | Percel et al. |
| 2003/0138495 A1 | 7/2003 | Jepsen |

FOREIGN PATENT DOCUMENTS

| | | |
|---|---|---|
| GB | 2 163 957 | 3/1986 |
| JP | 57-11912 | 1/1982 |
| JP | 57-58631 | 4/1982 |
| JP | 8-26977 | 1/1996 |
| JP | 2001-55322 | 2/2001 |
| WO | WO 91/16042 A1 | 10/1991 |
| WO | WO 92/11001 | 7/1992 |
| WO | WO 97/23199 A1 | 7/1997 |
| WO | WO 98/03161 A1 | 1/1998 |
| WO | WO 98/26767 | 6/1998 |
| WO | WO 99/21536 | 5/1999 |
| WO | WO 00/44353 | 8/2000 |
| WO | WO 01/66094 | 9/2001 |

OTHER PUBLICATIONS

French et al., "Evaluation of the Physicochemical Properties and Dissolution Characteristics of Mesalamine: Relevance to Controlled Intestinal Drug Delivery," *Pharmaceutical Research*, vol. 10, No. 9, pp. 1285-1290, 1993.

Gupta et al., "A novel pH- and time-based multi-unit potential colonic drug delivery system," International Journal of Pharmaceutics, vol. 213, pp. 83-91, 2001.

Office Action issued on Nov. 27, 2009 by the Examiner in U.S. Appl. No. 10/583,669 (US 2007/0154551).

Office Action issued on Aug. 17, 2010 by the Examiner in U.S. Appl. No. 10/583,669 (US 2007/0154551).

Office Action issued on May 3, 2011 by the Examiner in U.S. Appl. No. 10/583,669 (US 2007/0154551).

Office Action issued on Nov. 4, 2011 by the Examiner in U.S. Appl. No. 10/583,669 (US 2007/0154551).

Office Action issued on Feb. 14, 2012 by the Examiner in U.S. Appl. No. 10/583,669 (US 2007/0154551).

Notice of Allowance issued on Jun. 12, 2012 by the Examiner in U.S. Appl. No. 10/583,669 (US 2007/0154551).

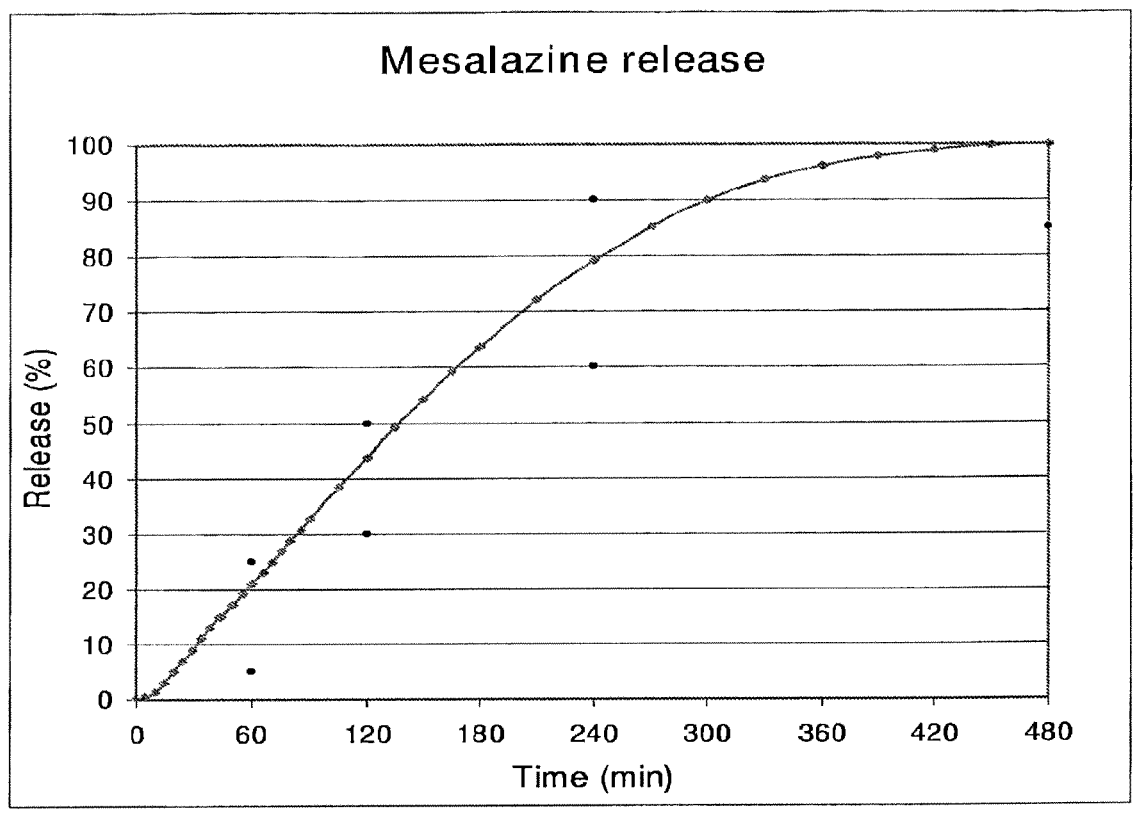

COATING METHOD

FIELD OF THE INVENTION

The present invention relates to a method for coating granules and the products obtainable by said method.

BACKGROUND

The literature describes coating methods wherein mixtures of EC (ethylcellulose) and HPMC (hydroxypropyl methylcellulose) are applied on spherical granules. Spherical granules comprising an active pharmaceutical ingredient (API) are conventionally obtained by spheronisation, including a spheronisation aid in the granules, or by coating non-pareil particles with API. The known methods are limited to be used for spherical granulate in order to reproducibly obtain a specific release profile.

There exists 250 mg PENTASA capsules on the US market. The capsules comprise a mixture of spherical pellets with a drug load of 66% mesalazine and non-pareil pellets. The mesalazine pellets are coated with an about 12 μm thick coating of EC, HPMC and acetylated monoglyceride. The capsule exhibits an approximately zero order release profile.

EP 540 813 A1 describes coating of spherical pellets comprising acetazolamide with a mixture of a water-insoluble film former such as ethylcellulose and a water-soluble film former such as hydroxypropyl methylcellulose to form a coating.

GB 2 163 957 A describes coating of pellets comprising theophylline with a mixture of ethylcellulose, hydroxypropyl methylcellulose and di-n-butylphthalate in a solvent comprising isopropanol, ethanol and water. The size of the pellets is defined by a diameter.

U.S. Pat. No. 5,188,841 describes spherical pellets coated with ethylcellulose and hydroxypropyl methylcellulose to obtain a modified release formulation. In vitro tests show an extended, approximately linear release rate for ketoprofen at typical physiological pH values.

There exists a need for a low-cost, reproducible method for coating granules irrespective of their shape or of irregular shapes on an industrial scale.

The present invention provides a coating method applicable for granulate independent on the shape of the granulate. It is especially suited for oblong or cylindric granulate obtained directly from an extruder. It provides a simple, cost-effective method for obtaining a controllable, e.g. a zero order, reproducible release profile on an industrial scale. The method has surprisingly shown to be suitable for an extruded mesalazine product, even with a high drug load.

DISCLOSURE OF THE INVENTION

The present invention provides a method for coating and the product obtainable by said method.

According to a preferred aspect, the present invention concerns a method for coating granules comprising mesalazine, with a coating mixture comprising two polymers, polymer I and polymer II;
said polymer I being selected to allow formation of a closing membrane around said granules in the absence of said polymer II, and said polymer II being selected to act as a water-soluble pore former in said coating mixture; wherein
a) the amount of polymer I is adjusted to provide a closing membrane in the absence of polymer II, and
b) the amount of polymer II in said coating mixture is adjusted to obtain coated granules which exhibit controlled release of mesalazine.

Controlled release implies gradual delivery of active substance, for mesalazine this may be measured according to the standard conditions defined below, usually providing less than 90% release after 15 minutes and more than 10% release after 8 hours. According to an aspect the invention provides for control of the release by altering the amount of polymer II in the coating mixture.

A water soluble pore former is a water soluble excipient which may be incorporated into a water insoluble coating membrane covering a composition comprising an API, said water soluble pore former dissolving in water and/or buffer whereby pores are formed in said coating membrane allowing release of the API.

According to an aspect, this method may be described as a two step method, wherein uncoated granules are used as a substrate. The method thus comprises:
A) The necessary amount of polymer I is adjusted by applying increasing amounts on the uncoated granules until a closing membrane is obtained, i.e. less than 10%, preferably less than 5% mesalazine is released at 8 hours. The release may preferably be measured according to the standard conditions described below.
B) Following a mixture of polymer I and polymer II is made. This mixture is applied on the uncoated granules, in an amount to ensure the amount of polymer I found in step A) is applied. The content of polymer II in the mixture is increased, until a zero order release profile is achieved.

According to an aspect, the present invention concerns a method, wherein a) the amount of polymer I is adjusted to the minimum necessary to provide a closing membrane in the absence of polymer II.

According to an aspect, the present invention concerns a method, wherein said obtained coated granules exhibit in vitro dissolution characteristics of mesalazine of
  a) between 5% and 25% at 1 hour;
  b) between 30% and 50% at 2 hours;
  c) between 60% and 90% at 4 hours; and
  d) not less than 85% dissolved at 8 hours;
as measured according to the standard conditions defined by stirring at 100 rpm in an apparatus 2 according to USP 24, in a 0.05 M pH 7.5 phosphate buffer prepared by dissolving 6.8 g monobasic potassium phosphate and 1 g sodium hydroxide in water to make 1000 mL of solution, and adjusting with 10 N sodium hydroxide to a pH of 7.50±0.05. These conditions will be referred to as "the standard conditions" for the purposes of the present invention.

According to an aspect, the present invention concerns a method, wherein said obtained coated granules exhibit in vitro dissolution characteristics of mesalazine of less than 25% at 15 minutes and not less than 60% dissolved at hours; as measured according to the standard conditions.

According to an aspect, the present invention concerns a method, wherein the coated granules exhibit an approximately zero order release profile of mesalazine until at least an amount of mesalazine selected among 40, 50, 60, 70, and 80%, preferably about 60%, is released.

The term "zero-order release" means a constant, linear, continuous, sustained and controlled release rate of API, i.e. the plot of mass of API released vs. time is linear. For practical applications the release of API may be approximated with a linear equation having a correlation factor of about 0.99 until 90% of the API is released.

The term "approximately zero order release" is used to denote that relative deviation, with respect to a zero-order release, of the released amount API up to a relative deviation selected among 20, 15, 10, 5, 3, 2, and 1%, may occur.

According to an aspect, the present invention concerns a method, wherein the coated granules have a similarity factor $f_2$ above 30, preferably above 40, more preferred above 50, as compared to a standard having the in vitro release characteristics of mesalazine of i) 20% released at 1 hour;
ii) 42% released at 2 hours;
iii) 77% released at 4 hours; and
iv) 100% released at 8 hours; as measured under the conditions stated above.

The similarity factor $f_2$ is defined by $$f_2 = 50 \log \{[1+(1/n)\Sigma_{t=1}^{n}(R_t-T_t)^2]^{-0.5} * 100\}$$

wherein n is the number of time points, R(t) is the mean percent active ingredient dissolved of the standard, and T(t) is mean percent active ingredient dissolved of the formulation according to the invention. The similarity factor is usually considered satisfactory if in the range 50-100, but may for the purposes of the present invention be even smaller, e.g. larger than 30 or 40.

According to an aspect, the present invention concerns a method, wherein the granules are non-spherical, preferably obtained by extrusion.

The coating according to the present invention is preferably applied to a granulate manufactured according to WO 03/032952 A1, U.S. application No. 60/464,649 or EP application 03388023.8. Such granulate has a surface especially suitable for a method according to the present invention.

According to an aspect, the present invention concerns a method, wherein the uncoated granules have an average aspect ratio of at least 1.1; preferably selected among 1.25-10; 1.3-5; 1.5-4.0; 1.7-3.7; 2.0-3.4; 2.2-3.2; 2.4-3.0; 2.6-2.8.

Uncoated granules having an average aspect ratio larger than one are easy to produce as they naturally result from extrusion. Further, extruded granules allow inclusion of a high drug load, as no spheronisation aid needs to be included in the composition.

The aspect ratio may be measured by spreading the granules on a flat surface and measuring from above the longest length of the individual granules as well as the width perpendicular to said longest length. The aspect ratio is defined as said longest length divided by said perpendicular width.

According to an aspect, the present invention concerns a method, wherein the average of the longest length of the granules is selected among 0.5-10; 1-8; 2-7; 3-6; and 4-5 mm. According to an aspect, the present invention concerns a method, wherein the average of said width of the granules is selected among 0.5-2; 0.6-1.8; 0.7-1.5; and 0.8-1 mm.

According to an aspect, the present invention concerns a method, wherein the fraction of the uncoated granules having sieve values of 1000-1180 is selected among 0-100%, 5-50%, 15-40%, 20-35%, 24-30%, and 26-28%. Unless otherwise mentioned, all fractions and ratios are in weight/weight.

Sieve values of 1000-1180 means the granules passes an 1180 sieve (1.180 mm) but are held back by a 1000 sieve.

According to an aspect, the present invention concerns a method, wherein the fraction of the uncoated granules having sieve values of 710-1000 is selected among 0-100%, 25-90%, 35-75%, 45-65%, 52-60%, and 55-57%.

According to an aspect, the present invention concerns a method, wherein the fraction of the uncoated granules having sieve values of 710-1180 is selected among 0-100%, 30-99*, 50-97%, 65-95%, 75-90%, 80-86%, and 82-84%.

Choosing the right sieve values is important for a number of reasons, including improving patient compliance. Very small and/or very large granules may be cumbersome to handle in production. Very small granules will often be associated with static electricity. Further, a uniform product may be difficult to obtain if there is a large spread of the particle sizes. It may especially be difficult to obtain a uniform coating giving the desired controlled release if the indicated range limits are not obeyed.

According to an aspect, the present invention concerns a method, wherein said polymer I is selected among ethylcellulose and polymethacrylate. Examples of polymethacrylates are Eudragit RL and RS.

According to an aspect, the present invention concerns a method, wherein said polymer I is ethylcellulose which is applied in an amount selected among 20-70, 30-65, 40-55, 45-50, 46-49, and 47-48 mg per g uncoated granules.

According to an aspect, the present invention concerns a method, wherein said polymer I is ethylcellulose which is applied in an amount adjusted, according to the specific surface area of the uncoated granules, to be selected among 0.74-0.81, 0.70-0.85, 0.60-0.90; 0.50-1.00, 0.40-1.10, and 0.30-1.20 mg/cm$^2$.

It has been discovered that the desired release profile may be obtained by adjusting the amount of coating material used according to the specific surface area.

The specific surface area may be measured by permeametry according to "Evaluation of a permeametry technique for surface area measurement of coarse particulate materials, International Journal of Pharmaceutics, Eriksson et al., 1990, 63, p. 189-199".

Granulate obtained according to co-pending patent application PCT/DK01/00677, is especially preferred, as is has a smooth surface facilitating measurement of specific surface area as well as subsequent coating.

In order to be able to determine the amount of coating that has to be applied to the granules the surface area is measured. Based on the measured correlation between the amount of coating per surface area and the dissolution rate profile, the amount of coating needed can be predicted from the measured surface area of the granules. The amount is adjusted by trial and error, as it depends on the exact conditions used, e.g. apparatus and excipients.

According to an aspect, the present invention concerns a method, wherein said polymer II is a water soluble polymer, such as HPMC or PEG (polyethylene glycol).

According to an aspect, the present invention concerns a method, wherein said polymer II is HPMC which is applied in an amount selected among 50-250, 75-225, 100-200, 125-190, 135-185, 150-180, 160-175, and 166-170 mg per g uncoated granules.

According to an aspect, the present invention concerns a method, wherein said polymer II is HPMC which is applied in an amount adjusted, according to the specific surface area of the uncoated granules, to be selected among 2.6-3.2, 2.4-3.4, 2.2-3.6, 2.0-3.8, 1.5-4.0, 1.0-5.0, and 0.5-6.0 mg/cm$^2$.

According to an aspect, the present invention concerns a method, wherein the weight ratio of said polymer I to said polymer II is selected among 1.5-8:1; 2-7:1; 3-6:1; 4-5:1 and about 4.5:1.

According to an aspect, the present invention concerns a method, wherein said coating mixture comprises 0.5-4%, preferably 1-3%, more preferred about 2%, polymer I.

According to an aspect, the present invention concerns a method, wherein said coating mixture comprises 6-8%, preferably 6.75-7.50%, most preferred about 7.00-7.25%, polymer II.

According to an aspect, the present invention concerns a method, wherein said coating mixture comprises a solvent selected among isopropanol, acetone, ethanol, water, a mixture of acetone and water, and a mixture of ethanol and water. The choice of solvent will depend on the choice of polymer I. Ethylcellulose is soluble in organic solvents such as ethanol, acetone, chloroform and toluene. Latex or pseudo-latex systems allow aqueous polymer dispersions of ethylcellulose such as Aquacoat or Surelease may be used to produce ethylcellulose films without the need for organic solvents. Aqueous ethyl cellulose dispersions are environmentally advantageous and safe, but necessitate higher drying capacity during coating. Further, additives may be necessary in the coating dispersion which may increase the weight of the coated product.

According to an aspect, the present invention concerns a method, wherein said coating mixture further comprises a plasticizer, preferably acetylated monoglyceride. A plasticizer may improve the reproducibility of the product preparation. According to an aspect, the present invention concerns a method, wherein said plasticizer is acetylated monoglyceride which is applied in an amount selected among 1-20, 2-15, 3-10, and 4 mg per g uncoated granules. The preferred amount is 4 mg per g uncoated granules. According to an aspect, the present invention concerns a method, wherein said plasticizer is acetylated monoglyceride which is applied in an amount adjusted, according to the specific surface area of the uncoated granules, to be selected among 0.063-0.077, 0.060-0.080, 0.055-0.085, 0.050-0.090, 0.040-0.10, 0.030-0.11, and 0.020-0.12 mg/cm$^2$.

According to an aspect, the present invention concerns a method, wherein the thickness of said coating mixture of said coated granules is selected among 5-100, 10-80, 12-60, 14-40, 15-36, 16-33, 17-30, 18-27, 19-25, 20-24, 21-23, and about 22 μm. The thickness is preferably larger than 13 μm to ensure uniform coating of the granules.

The thickness of the coating membrane may be measured on a granulate by measuring on three granules and taking the average of five different measurements made on each granule. The measurements may be made on cross sectional images of the granules with SEM (Scanning Electron Microscopy).

According to an aspect, the present invention concerns a method, wherein said granules comprise at least 40, preferably at least 50, more preferred at least 60, preferably at least 70, more preferred at least 80, preferably 85-99, more preferred 90-98, preferably 93-97, more preferred 94-96, most preferred about 95, weight % mesalazine.

Such granules and their manufacture have been described in WO 03/032952 and more specifically in U.S. application No. 60/464,649 and EP 03388023.8.

According to an aspect, the present invention concerns a method, wherein said granules comprises a pharmaceutically acceptable binder selected among acacia, gelatine, hydroxypropyl cellulose, hydroxypropylmethyl cellulose, methylcellulose, polyethylene glycol (PEG), povidone, sucrose, starch, and a mixture of any of these. Povidone (polyvinylpyrrolidone, PVP) is preferred.

According to an aspect, the present invention concerns a method, wherein said granules comprises a pharmaceutically acceptable binder, in an amount selected among the group consisting of 1-10, 2-8, 3-7, 4-6 and about 5% by weight.

The granulate may optionally comprise at least one further additive selected from a disintegrating agent, binder, lubricant, flavoring agent, preservative, and a colorant. Representative examples can be found in "*Handbook of Pharmaceutical Excipients*", Ed. A. H. Kibbe, 3$^{rd}$ Ed., American Pharmaceutical Association, USA and Pharmaceutical Press UK, 2000.

According to an aspect, the present invention concerns the product obtainable by the method according to any other aspect of the present invention. According to an aspect, the present invention concerns said product being in a presentation form selected among a sachet, a caprule, and a tablet; preferably a sachet. According to an aspect, the present invention concerns said product comprising a total amount of mesalazine chosen among the group consisting of 0.250, 0.5, 1.0, 1.5, 2, 3, 4, 5, 6, 8, and 10 g.

According to an aspect, the present invention concerns the use of mesalazine for the manufacture of said product for the treatment of intestinal bowel disease, preferably Crohn's Disease or Ulcerative Colitis.

According to an aspect, the present invention concerns a method for the treatment of intestinal bowel disease, preferably Crohn's Disease or Ulcerative Colitis, comprising administering said product.

The following examples are provided to elucidate rather than limit the present invention.

EXAMPLE

A batch of uncoated granules was provided as follows as calculated per 100 kg of mesalazine:

| Constituents | Quantity | Specification |
| --- | --- | --- |
| Mesalazine | 100 kg | Ferring |
| Povidone | 5 kg | Ph. Eur. |
| Water, purified | 18.4 kg* | Ph. Eur. |

*Evaporates during production

The manufacturing method of the uncoated granules follows closely the manufacturing method described in co-pending patent applications U.S. Pat. No. 60/464,649 and EP No. 03388023.8.

The manufacturing process for the uncoated granules can be divided into 6 steps:
1. Preparation of granulation liquid
2. Granulation of Mesalazine with water and PVP
3. Extrusion
4. Fluid bed drying
5. Milling
6. Sieving

| Equipment for the production | Function |
| --- | --- |
| NICA Extruder E220 | Extrusion |
| Rotostat T05 | Blending |
| NIRO Fluid bed dryer | Drying |
| Quadro Comil U10 | Milling |
| Mogensen sieve | Sieving |

Step 1:
For one batch of granulation liquid water is filled into a Müller drum. The mixer is put into position and started. Polyvinylpyrrolidone (PVP) is slowly sprinkled onto the water and the mixer is allowed to run a fixed time until all PVP is dissolved.

Step 2 and 3:
Mesalazine is placed in a vibrating Prodima hopper and by the use of a conveyor the mesalazine is transported up to a weight belt feeder dosing the mesalazine into the continuous Niro line. In the first part of the Niro line the mesalazine and the water solution of PVP are mixed to a wet mass before being transported into the extruder. After extrusion of the wet mass of mesalazine and PVP/water through a screen mesh 0.9 mm, the granules fall directly into the fluid bed dryer.

Step 4:

The fluid bed dryer is divided into two main sections. In the first section, the granules are dried on the surface to prevent them from sticking together. In this section of the fluid bed, a random mixing of the granules takes place. After a certain residence time, the granules are moved into the second part of the dryer where the actual drying takes place. In the second part of the dryer the granules are guided by the use of the drying air through the dryer. When the granules are dry they are allowed to fall into a drum placed under the fluid bed. The fluid bed is constructed in such a way that the overall dwelling time in the fluid bed is approximately 2½ hours.

Step 5:

The drums containing the dry granules are placed upside down on top of the mill and the granules are gently milled using a screen, which will only break the granules which are exceedingly long. After passing the mill, the granules are allowed to fall into a drum.

Step 6:

Due to the fact that the milling process generates a small amount of undersized granules, the granules are sieved using a Mogensen vibration sieve. Granules, which pass the screen 0.8 mm, are discarded or can be collected for reprocessing stored in airtight, labelled containers.

A batch of coated granules was manufactured using the uncoated mesalazine granules as described above. The coated granules were provided as follows:

| Constituents | Quantity |
|---|---|
| Uncoated mesalazine granules | 500 g |
| Acetone | 1035.7 g* |
| Water, purified | 54.5 g* |
| Ethylcellulose | 24.0 g |
| Hydroxypropylmethylcellulose | 84.0 g |
| Acetylated monoglyceride | 1.8 g |

*Evaporates during production

The manufacturing process for coating of the granules can be divided into 3 steps:
1. Preparation of granulation liquid
2. Coating
3. Drying

| Equipment for production | Function |
|---|---|
| IKAMAG magnetic stirrer | Blending |
| Strea-1 coater | Coating |
| Memmert heating cabinet | Drying |

Step 1:

For one batch of coating liquid the solvent mixture of acetone/water (95/5) is filled into a beaker. Ethylcellulose, hydroxypropyl methylcellulose and acetylated monoglyceride is separately added to the solvent one at a time while stirring with a magnetic stirrer. The coating liquid is left to stand stirring overnight.

The amount of ethylcellulose is adjusted to the minimum necessary to provide a closing membrane in the absence of HPMC, while the amount of HPMC in the coating mixture is adjusted to obtain coated granules which exhibit controlled release of mesalazine.

Step 2:

500 g of sieved granules are coated in a Strea-1 laboratory coater with a coating liquid consisting of ethyl cellulose, hydroxypropyl methylcellulose and acetylated monoglyceride dissolved in a mixture of acetone and water (95/5).

Air volume: 45-50 m³/h
Atomizing pressure: 1.5 bar
Blow out pressure: 5 bar
Drying temperature: 70° C.
Pump speed: 23 g/l Step 3:

After the coating process, the coated granules are loaded onto a tray and placed in an oven for drying for 24 hours at 90° C.

Following this manufacturing procedure the batch gave granulate with the following approximate composition:

| | |
|---|---|
| Mesalazine | 78.1% |
| Povidone | 3.9% |
| Ethylcellulose | 3.9% |
| Hydroxypropyl methylcellulose | 13.8% |
| Acetylated monoglyceride | 0.3% |

FIGURES

FIG. 1 depicts the release of mesalazine, as measured according to the standard conditions, from the product resulting from the experimental procedure above.

All the cited references are hereby incorporated in their entirety.

The invention claimed is:

1. A method for making a pharmaceutical product comprising mesalazine, comprising:
    coating an uncoated mesalazine composition with a coating mixture comprising ethyl cellulose and hydroxypropyl methylcellulose, thereby obtaining a mesalazine composition coated with a single coating layer; wherein
    (a) the amount of ethyl cellulose in said coating mixture is an amount that would be effective to provide a closing membrane around said composition in the absence of said hydroxypropyl methylcellulose, and
    (b) the amount of hydroxypropyl methylcellulose in said coating mixture is 50-250 mg per g uncoated composition,
    wherein said mesalazine composition coated with a single coating layer exhibits controlled release of mesalazine and in vitro dissolution characteristics of mesalazine of
    between 5% and 25% at 1 hour;
    between 30% and 50% at 2 hours;
    between 60% and 90% at 4 hours; and
    not less than 85% dissolved at 8 hours;
    as measured by stirring at 100 rpm in apparatus 2 according to USP 24, in a 0.05 M pH 7.5 phosphate buffer prepared by dissolving 6.8 g monobasic potassium phosphate and 1 g sodium hydroxide in water to make 1000 mL of solution, and adjusting with 10 N sodium hydroxide to a pH of 7.50±0.05; and
    preparing a pharmaceutical product comprising said mesalazine composition coated with a single coating layer.

2. The method of claim 1, wherein the uncoated mesalazine composition is in the form of granules.

3. The method of claim 1, wherein the uncoated mesalazine composition is in the form of pellets.

4. The method of claim 1, wherein the uncoated mesalazine composition is in the form of particles.

5. The method of claim 1, wherein the coating mixture further comprises a solvent comprising ethanol.

6. The method of claim 1, wherein the uncoated mesalazine composition comprises from 90-98% by weight mesalazine.

7. The method of claim 1, wherein the uncoated mesalazine composition comprises from 93-97% by weight mesalazine.

8. The method of claim 1, wherein the uncoated mesalazine composition comprises from 94-96% by weight mesalazine.

9. The method of claim 1, wherein the uncoated mesalazine composition further comprises a pharmaceutically acceptable binder.

10. The method of claim 9, wherein the pharmaceutically acceptable binder comprises povidone.

11. The method of claim 1, wherein the pharmaceutical product is selected from the group consisting of a sachet, a capsule, and a tablet.

12. A pharmaceutical product made by a method according to claim 1.

13. The pharmaceutical product according to claim 12, in a form selected from the group consisting of a sachet, a capsule, and a tablet.

14. The pharmaceutical product according to claim 12, in the form of a sachet.

15. The pharmaceutical product according to claim 12, in the form of a capsule.

16. The pharmaceutical product according to claim 12, in the form of a tablet.

17. The pharmaceutical product according to claim 12, comprising a total amount of mesalazine selected from the group consisting of 0.250, 0.5, 1.0, 1.5, 2, 3, 4, 5, 6, 8, and 10 g.

18. A medicament comprising the pharmaceutical product according to claim 12, comprising an amount of mesalazine effective for the treatment of intestinal bowel disease, Crohn's Disease or Ulcerative Colitis.

* * * * *